US011878075B2

(12) United States Patent
Bharate et al.

(10) Patent No.: US 11,878,075 B2
(45) Date of Patent: Jan. 23, 2024

(54) SUSTAINED RELEASE FORMULATIONS OF DYSOXYLUM BINEFACTERUM

(71) Applicant: COUNCIL OF SCIENTIFIC AND INDUSTRIAL RESEARCH, New Delhi (IN)

(72) Inventors: Sonali Sandip Bharate, Jammu (IN); Vikas Kumar, Jammu (IN); Mehak Gupta, Jammu (IN); Sumit Gandhi, Jammu (IN); Ajay Kumar, Jammu (IN); Sandip Bibishan Bharate, Jammu (IN); Ram Vishwakarma, Jammu (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 100 days.

(21) Appl. No.: 17/046,007

(22) PCT Filed: Apr. 18, 2019

(86) PCT No.: PCT/IN2019/050313
§ 371 (c)(1),
(2) Date: Oct. 8, 2020

(87) PCT Pub. No.: WO2019/202610
PCT Pub. Date: Oct. 24, 2019

(65) Prior Publication Data
US 2021/0137841 A1      May 13, 2021

(30) Foreign Application Priority Data

Apr. 19, 2018   (IN) .............................. 201811014818

(51) Int. Cl.
*A61K 9/16* (2006.01)
*A61K 36/58* (2006.01)

(52) U.S. Cl.
CPC .......... *A61K 9/1635* (2013.01); *A61K 9/1652* (2013.01); *A61K 36/58* (2013.01)

(58) Field of Classification Search
None
See application file for complete search history.

(56) References Cited

U.S. PATENT DOCUMENTS 9,776,989 B2 * 10/2017 Vishwakarma ......... A61P 35/00
2016/0046611 A1 * 2/2016 Vishwakarma ......... A61P 29/00
546/196

OTHER PUBLICATIONS

Kumar et al., Anti-inflammatory chromone alkaloids and glycoside from Dysoxylum binectariferum. Tetrahedron Letter. vol. 58, Issue 42, Oct. 18, 2017, pp. 3974-3978 (Year: 2017).*

(Continued)

*Primary Examiner* — Lakshmi S Channavajjala
(74) *Attorney, Agent, or Firm* — Blank Rome LLP

(57) ABSTRACT

The present invention relates to the novel formulation for sustained or delayed release of rohitukine-rich *Dysoxylum binectariferum* extract/fraction and a process for preparing the same wherein the extract is wet-granulated using excipients i.e. biodegradable polymers and/or non-biodegradable polymers alone or in combination, and the said granules are either filled into a capsule or compressed into a tablet. The said formulation comprising a granulated extract/fraction of rohitukine-rich *Dysoxylum binectariferum* with polymers has resulted in a sustained release of the extract or fraction over a period of 16-24 hrs. The said formulations are useful in the treatment of inflammatory diseases.

14 Claims, 6 Drawing Sheets

(56) References Cited

OTHER PUBLICATIONS

Mahajan et al., Production of rohitukine in leaves and seeds of Dysoxylum binectariferum: An alternate renewable resource. Pharmaceutical Biology, 2015:53(3):446-450 (Year: 2015).*
Jain et al., Isolation and biological evaluation of chromone alkaloid dysoline, a new regioisomer of rohitukine from Dysoxylum binectariferum. Tetrahedron Letter 2013, 7140-7143. (Year: 2013).*
Giunchedi et al., Evaluation of Alginate Compressed Matrices as Prolonged Drug Delivery Systems. (AAPS PharmSci Tech, 2000; 1(3) article 19 (Year: 2000).*
Nayak et al., Formulation and in vitro evaluation of Hydrodynamically balanced system for theophylline delivery. Journal of Basic and Clinical Pharmacy. pp. 133-137. available online Aug. 15, 2011 (Year: 2011).*
James S. Blachly MD, et al., "Cyclin Dependent Kinase Inhibitors for the Treatment of Chronic Lymphocytic Leukemia", http://dx.doi.org/10.1053/j.seminoncol.2016.02.003.
Ryan D. Cassaday et al., "A Phase II, Single-Arm, Open-Label, Multicenter Study to Evaluate the Efficacy and Safety of P276-00, a Cyclin-Dependent Kinase Inhibitor, in Patients With Relapsed or Refractory Mantle Cell Lymphoma", Clinical Lymphoma, Myeloma & Leukemia, vol. 15, No. 7, 392-7, 2015.
Yashpal S. Chhonker et al., "Pharmacokinetic and metabolism studies of rohitukine in rats by high performance liquid-chromatography with tandem mass spectrometry", http://dx.doi.org/10.1016/j.fitote.2014.5.004; 2014.
Y.S. Chhonker et al., "Pharmacokinetics, Tissue Distruction and Plasma Protein Binding Studies of Rohitukine: A Potent Antihyperlipidemic Agent", Drug Res 2015; 65: 380-387.
Alan D. Harmon et al., "The Structure of Rohitukine, The Main Alkaloid of Amoora Rohituka (Syn. Aphanamixis Polystachya) (*Meliaceae*)", Tetrahedron Letters No. 8, pp. 721-724, 1979.
Govind Keshri et al., "Contraceptive and hormonal properties of the stem bark of Dysoxylum binectariferum in rat and docking analysis of rohitukine, the alkaloid isolated from active chloroform soluble fraction", Contraception 76 (2007) 400-407.
V. Lakshmi et al., "In vitro and in vivo leishmanicidal activity of Dysoxylm binectariferum and its fractions against Leishmania donovani", Phytomedicine 14 (2007) 36-42.
Sunil K. Mishra et al., "Pharmacological evaluation of the efficacy of Dysoxylum binectariferum stem bark and its active constitutent rohitukine in regulation of dyslipidemia in rats", J Nat Med, DOI 10.1007/s11418-014-0830-3.
Patel Mohanakumara et al., "Dysoxylum binectariferum Hook.f (*Meliaceae*), a rich source of rohitukine", Fitoterapia 81 (2010) 145-148.
P. Mohana Kumara et al., Ambient ionization mass spectrometry imaging of rohitukine, a chromone anti-cancer alkaloid, during seed development in Dysoxylum binectariferum Hook.f (*Meliaceae*), Phytochemistry xxx (2015) xxx-xxx.
Ali Nokhodchi et al., "The Role of Oral Controlled Release Matrix Tablets in Drug Delivery Systems", BioImpacts, 2012. 2(4), 175-187; doi: 10.5681/bi.2012.027; http://bi.tbzmed.ac.ir/.
Safia et al., "The Chromone Alkaloid, Rohitukine, Affords Anti-Cancer Activity via Modulating Apoptosis Pathways via Modulating Apoptosis Pathways in A549 Cell Line and Yeast Mitogen Activated Protein Kinase (MAPK) Pathway", PLOS One, DOI:10.1371/journal.pone.0137991, Sep. 25, 2015.
Neetu Singh et al., "Gastroprotectice effect of anti-cancer compoun rohitukine: possible role of gastrin antagonism and H+ K+-ATPase inhibition", Naunyn-Schmiedeberg's Arch Pharmacol (2012) 385:277-286, DOI 10.1007/s00210-011-0711-1.
Salil Varshney et al., "Rohitukine inhibits in vitro adipogenesis arresting mitotic clonal expansion and improves dyslipidemia in vivo", Journal of Lipid Research, vol. 55, 2014.
Peter J. Wiernik et al., "Alvocidib (flavopiridol) for the treatment of chronic lymphocytic leukemia", ISSN: 1354-3784 (Print) 1744-7658 (Online) Journal homepage: http://www.tandfonline.com/loi/ieid20.

* cited by examiner

A

SUSTAINED RELEASE FORMULATIONS OF DYSOXYLUM BINEFACTERUM

CROSS REFERENCE TO RELATED APPLICATIONS

This application is a national phase of PCT application No. PCT/IN2019/050313, filed Apr. 18, 2019, which claims priority to IN patent application No. 201811014818, filed Apr. 19, 2018, all of which are incorporated herein by reference thereto.

FIELD OF THE INVENTION

The present invention relates to novel oral formulations for sustained or delayed release of rohitukine-rich *Dysoxylum binectariferum* extract/fraction and a process for preparing the same. In particular, the present invention relates to the novel formulations which form a matrix in gastrointestinal tract and give sustained release of active ingredient rohitukine up to 24 hrs. Sustained release formulation increases the efficacy of active ingredient rohitukine which has a short biological half-life. The said formulations are useful for the treatment of rheumatoid arthritis and other inflammatory diseases.

BACKGROUND OF THE INVENTION

Oral sustained release dosage forms are very efficient for the delivery of drugs required in the multiple dose regimens because of their short elimination half-life. A sustained release dosage form reduces the dosage frequency and also reduces the sudden high plasma exposure of hydrophilic drugs. After oral administration, the controlled release of the drug results in its prolonged systemic availability (Nokhodchi et al., *BioImpacts* 2012, 2,175). The sustained release dosage form results in a steady and safer therapeutic concentration of drug in plasma. In this way, this drug delivery system improves patient compliance and results in successful treatment. Sustained release dosage form is a type of extended release dosage form which can be of three types: (a) monolithic or matrix system, (b) reservoir or membrane controlled system, and (c) osmotic pump system. These systems comprises of two components i.e. active drug and release controlling agent (matrix/membrane former). In monolithic matrix system, drug/drug particles are dispersed in a polymer matrix, which may or may not be water soluble. These matrices either slowly erode or swell in water to release the active drug substance.

*Dysoxylum* is a flowering plant genus of trees and shrubs, belonging to the Meliaceae family. *Dysoxylum binectariferum* is indigenous to India. Fruits of this plant possess anti-inflammatory, diuretic, and CNS depressant activities. The stem bark, fruits and leaves of this plant contains an alkaloid, rohitukine as a major constituent. Rohitukine, a chromone alkaloid, first isolated from *Amoora rohituka* (Roxb.) and later from various parts of *Dysoxylum binectariferum* Hook (Harmon et al., *Tetrahedron Lett.* 1979, 8, 721; and Mohanakumara et al., *Fitoterapia* 2010, 81, 145). It shows cytotoxic properties against lung cancer cells (A549) and budding yeast (Safra et al., *PLOS One* 2015, 10, e0137991). It is also reported to possess several other pharmacological activities including antiadipogenic (Varshney et al., *J. Lipid Res.* 2014, 55, 1019), antidyslipidemic (Mishra et al., 2014, *J. Nat. Med.* DOI: 10.1007/s11418-014-0830-3), antifertility (Keshri et al., *Contraception* 2007, 76, 400), gastroprotective (Singh et al., *Arch. Pharmacol.* 2011, 385, 277) and antileishmanial activities (Lakshmi et al., *Phytomedicine* 2007, 14, 36). Rohitukine has led to the discovery of two anticancer clinical candidates viz. flavopiridol (Blachly et al., *Semin. Oncol.* 2016, 43, 265, and Wiernik P. H. *Expert Opin. Investig. Drugs* 2016, 25, 729) and P276-00 (Cassaday et al., *Clin. Lymphoma Myeloma Leuk.* 2015, 15, 392).

The chemical structures of these candidates are given below.

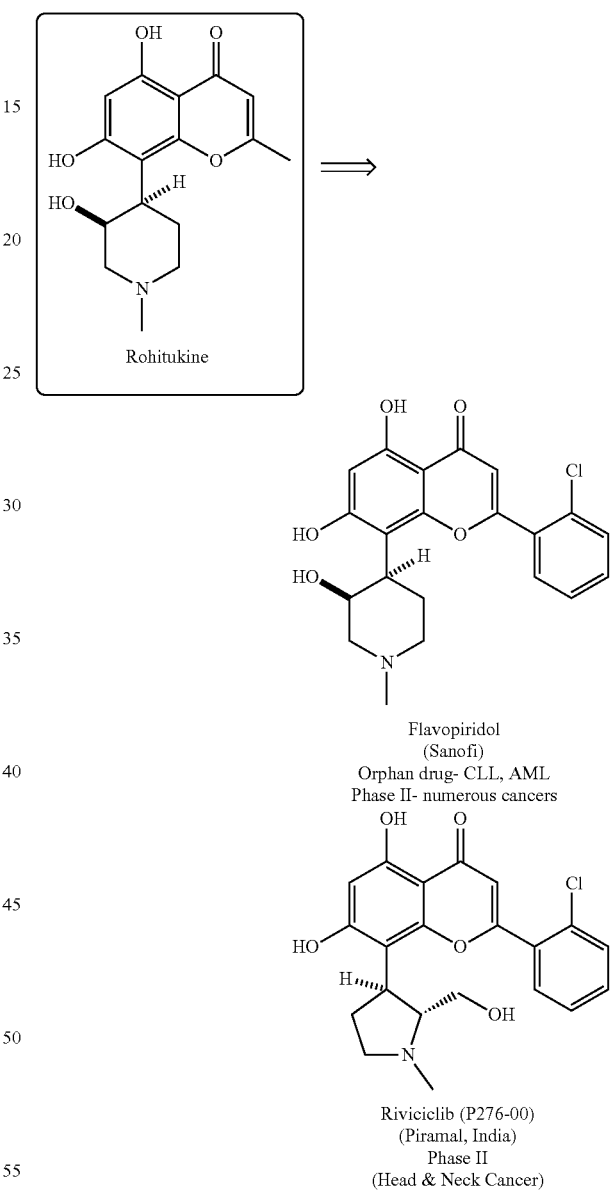

Flavopiridol (Sanofi)
Orphan drug- CLL, AML
Phase II- numerous cancers

Riviciclib (P276-00)
(Piramal, India)
Phase II
(Head & Neck Cancer)

Rohitukine is present in all parts of the plant including stem bark, trunk bark, fruits and leaves (Mohana Kumara, P. et al., *Phytochemistry* 2015, 116, 104; and Mahaj an V. et al., *Pharm. Biol.* 2015, 53, 446). Leaves of *D. binectariferum* contain about 1% rohitukine. Furthermore, bioanalytical methods and pharmacokinetic analysis of rohitukine has also been reported (Chhonker, Y. S. et al., *Fitoterapia* 2014, 97, 34; Chhonker, Y. S. et al., Drug Res. (Stuttg) 2015, 65, 380). Pharmacokinetic study of rohitukine in rats has shown that it undergoes rapid elimination after oral and intravenous administration and thus has short biological half-life (1-2 h) (Chhonker, Y. S. et al., *Fitoterapia* 2014, 97, 34).

Rohitukine, a major bioactive constituent of *Dysoxylum binectariferum*, despite of its interesting biological activities has a rapid elimination from the body which results in its decreased efficacy and needs to be compensated by increased dosing frequency to make the treatment effective. Furthermore, the conventional formulations of herbal extracts have difficulty in filling into capsules because of their characteristic strong hygroscopicity. Therefore in view of the above there is a need to develop formulation of *Dysoxylum binectariferum* to overcome the existing drawbacks.

OBJECTIVES OF THE INVENTION

The objective of this invention is to provide a new oral formulations of rohitukine-rich extract of *Dysoxylum binectariferum* that will reduce the dosing frequency.

Another objective of the invention is to provide an oral sustained release formulation for delayed release of the active ingredient over the period of up to 16 to 24 hrs.

Another objective of the invention is also to provide the rohitukine-enriched fraction for improved therapeutic efficacy.

It is also an objective of this invention to provide novel sustained release formulations containing elevated concentrations of at least one of specific markers obtained by means of the process.

It is another objective of this invention to provide the use and method of application of this formulation for treatment of inflammatory diseases involving elevated levels of proinflammatory cytokines.

SUMMARY OF THE INVENTION

The oral sustained release formulation according to one exemplary embodiment of the present invention comprises rohitukine-rich extract of leaves of *Dysoxylum binectariferum* (Family: Meliaceae). The "rohitukine-rich extract/fraction of *Dysoxylum binectariferum*" is characterized for the content of rohitukine ($C_{16}H_{19}NO_5$, molecular weight=305.33), and schumaniofioside A ($C_{16}H_{18}O_9$, molecular weight=354.15) which should comprise at least 2% w/w and 1%, respectively.

In one preferred embodiment of the present invention, a sustained release formulation comprising granules of rohitukine-rich *Dysoxylum binectariferum* extract or enriched fraction; biodegradable polymers and/or non-biodegradable polymers, alone or in combination; and optionally an excipient, selected from carrier, adjuvant and binder; wherein the extract or fraction comprises of at least rohitukine and schumaniofioside A.

In one preferred embodiment of the present invention, said extract is hydroalcoholic extract.

In another preferred embodiment of the present invention, said fraction is soluble portion of methanol:acetone system of the hydroalcholic extract.

In one preferred embodiment of the present invention, the biodegradable polymers and/or non-biodegradable polymers alone or in combination are selected from the group consisting of hydroxypropylmethylcellulose K4M, hydroxypropylmethylcellulose K15M and sodium alginate.

In one preferred embodiment of the present invention, said rohitukine-rich *Dysoxylum binectariferum* extract/fraction comprises at least 2% w/w of rohitukine along with at least 1% of schumaniofioside A.

In one preferred embodiment of the present invention, said formulation comprises at least 30-60% w/w of rohitukine-rich *Dysoxylum binectariferum* extract or fraction, 25-50% w/w hydroxypropylmethylcellulose, and 5-15% w/w of sodium alginate.

In one preferred embodiment of the present invention, the total in-vitro dissolution time of said formulations required for release of 60-80% of active ingredients provides the sustained release of rohitukine in gastrointestinal tract is between for about 16-24 hours.

In one preferred embodiment of the present invention, a process of preparing said formulations, comprising the steps of:

i. mixing powdered plant drug with an extracting hydroalcoholic solution in the proportion of 1:1, using ethanol as alcohol, in the initial proportion of 1 part plant ingredient to 5-10 parts of hydro-alcoholic solution to obtain hydroalcoholic mixture, ii. performing an extraction for a period of at least 3 hours at 20-30° C. in a closed reactor under mechanical stirring to obtain residue and hydroalcoholic extract, iii. extracting the residue of step-ii by repeating the process of step-i and further re-extracting to obtain residue and hydroalcoholic extract, iv. combining the hydro-alcoholic extracts of step ii and iii, concentrating by vacuum assisted evaporation at temperature of 40° C., vacuum of 250 mm Hg until the mass corresponds to approximately 25% of the mass, following up by drying of concentrated mixture through freeze-drying to obtain dry powder of hydroalcoholic extract, v. dissolving the powdered hydroalcoholic extract as obtained in step iv in 50:50 v/v methanol:acetone system and mixture stirred for 3 hours to obtain soluble portion of fraction and residue of hydroalcoholic extract, vi. extracting the residue of step-v by repeating the process of step-v and further re-extracting to obtain the residue and soluble portion of fraction, vii. combining soluble portions of fraction obtained in step v and vi, concentrating by vacuo rotavapor to obtain dry powder of fraction, viii. mixing the rohitukine-rich *Dysoxylum binectariferum* extract/fraction obtained in step iv and/or vii, and polymers in geometric proportion to obtain uniformly mixed powder, ix. adding a binder solution to the uniformly mixed powder to obtain a wet-mass x. passing of the wet-mass of step ix through a sieve of mesh size #10-12 and retaining on a sieve of mesh size #30-35 to obtain granules, xi. drying of the granules obtained in step x, in hot air oven at 40-60° C. temperature for 1-2 hrs to obtain polymeric granules, and xii. filling of the polymeric granules of *Dysoxylum binectariferum* extract or fraction in two-piece hard gelatin capsules to obtain sustained release formulations of claim 1.

In one preferred embodiment of the present invention, the binder is selected from the group consisting of polyvinylpyrrolidone K 30, and polyvinylpyrrolidone K 15.

In one preferred embodiment of the present invention, the binder solution is prepared by dissolving the binder mentioned in isopropyl alcohol as 5-10% w/v.

In one preferred embodiment of the present invention, said formulation is useful in treating inflammatory conditions wherein proinflammatory cytokines (including TNF-alpha, interleukin-6) are involved.

In one preferred embodiment of the present invention, the inflammatory conditions comprise rheumatoid arthritis, cystic fibrosis, atherosclerosis and cancer.

In one preferred embodiment of the present invention, said formulation is in the form selected from the group consisting of a hard gelatin capsule or a tablet.

There is provided a novel drug delivery composition for the controlled release of an active ingredient in the gastrointestinal tract over a prolonged period of time. In particular, there is provided a novel sustained release oral formulations of *Dysoxylum binectariferum* for supplying optimum plasma concentrations of the biologically active compound "rohitukine". These novel formulations are hydrophilic matrix based delivery systems which usually work by diffusion rate control mechanism. These dosage forms prolong the release of rohitukine from the matrix, resulting in its controlled systemic exposure.

The novel drug release system according to one exemplary embodiment of the present invention is achieved by the use of the pharmaceutical composition comprising the "rohitukine-rich *Dysoxylum binectariferum* extract or fraction" in combination with one or more sustained release polymers.

In one preferred embodiment of the invention, the orally-administrable formulation for the controlled release of active ingredient 'rohitukine' comprises granulated rohitukine-rich *Dysoxylum binectariferum* extract and at least one excipient, and is characterized in that the total in vitro dissolution time of the formulation required for the release of 100% of the active ingredient available from the formulation, is between about 16-24 hrs, as determined by the U.S.P. dissolution apparatus by Basket method at a speed of 50 rpm, and temperature of 37° C.±0.5, using 900 ml of dissolution media (pH 1.2 and pH 6.8 buffers).

In one preferred embodiment of the invention, the sustained release formulation is characterized in that it contains at least 1% w/w of rohitukine and 0.5% of schumaniofioside A.

In another preferred embodiment of the invention, the formulation is in the form selected from the group consisting of a matrix tablet or a hard gelatin two-piece capsule filled with polymeric granules or microparticles of granulated extract.

The invention also comprises a process for the preparation of an orally-administrable formulation for the controlled release of granulated extract. The steps for preparation of said formulation comprising rohitukine-rich *Dysoxylum binectariferum* extract, hydroxypropylmethylcellulose K15M, and sodium alginate comprises:

a) extraction of dried powdered material of *Dysoxylum binectariferum* (leaves) with ethanol:water (1:1) to yield an extract solution;

b) concentrating the extract solution first by vacuum drying followed by freeze drying to yield dry powder. The extractive value of hydroalcoholic extract (A002-A) on dry weight basis is found to be 18-25% w/w.

Further enrichment of the rohitukine-content in the obtained extract was done using following steps:

c) stirring the dried hydroalcoholic extract in the solution of methanol:acetone (1:1) at room temperature (25-30° C.) for 3 h×2 times. The total volume of solvent mixture used was 10 ml/g of dried extract.

d) concentrating the methanol:acetone soluble layer as obtained in step 'c' by vacuum drying to yield dry powder of rohitukine-enriched fraction. The extractive value of rohitukine-enriched fraction (A002-AEF) from powdered plant material (on dry weight basis) is found to be 9-12% w/w (45-50% w/w from A002-A).

The SR formulations of the rohitukine-rich *Dysoxylum binectariferum* extract were prepared using following steps:

e) mixing the rohitukine-rich *Dysoxylum binectariferum* extract/fraction (containing at least 2% w/w of rohitukine and 1% of schumaniofioside A) with excipient(s) in mortar and pestle, following by addition of 10% PVP-K30 solution in isopropanol (as a binder) to form a dough.

f) passing of a wet-mass through a stainless steel sieve of mesh size #10.

g) drying of granules in hot air oven at 50° C. for 30-60 min.

h) passing of dried granules through sieve #10 and retaining on sieve #30.

i) filling of polymeric granules of *Dysoxylum binectariferum* extract/fraction in two-piece hard gelatin capsules.

In another aspect of the present invention, a method for enrichment of one of the active constituent is provided.

In one more embodiment of the invention, the standardization of the rohitukine-rich *Dysoxylum binectariferum* extract/fraction is provided to identify and quantify the amount of specified marker compounds in the extract/fraction by HPLC.

In another embodiment of the invention, standardized rohitukine-rich *Dysoxylum binectariferum* extract/fraction displayed significant inhibition of proinflammatory cytokines in human monocytic THP-1 cells.

In another embodiment of the invention, standardized rohitukine-rich *Dysoxylum binectariferum* extract/fraction displayed significant inhibition of proinflammatory cytokine TNF-alpha in LPS induced septic shock model in BALB/C mice.

In another embodiment of the invention, standardized rohitukine-rich *Dysoxylum binectariferum* extract/fraction displayed significant inhibition of proinflammatory cytokine TNF-alpha and IL-6 in in collagen induced arthritis model in DBA/1J mice.

In one particular aspect of the present invention, rohitukine-rich *Dysoxylum binectariferum* extract/fraction is provided, which comprises active components for cytokine inhibition, and related manifestations and disorders along with a pharmaceutically acceptable carrier, and methods of using the same. Accordingly, the present invention is directed generally to the sustained release formulations of standardized rohitukine-rich *Dysoxylum binectariferum* extracts for treatment of inflammatory diseases wherein proinflammatory cytokines are involved.

In another aspect of the invention, inflammatory diseases comprise rheumatoid arthritis and related disorders in humans and other mammals.

In further embodiment of the present invention, a method of treatment of mammals afflicted with the inflammatory diseases comprises rheumatoid arthritis, cystic fibrosis, atherosclerosis and cancer, comprising administering the claimed sustained release formulations or optionally along with the other medicinally active agents.

ABBREVIATIONS

Figure 1:
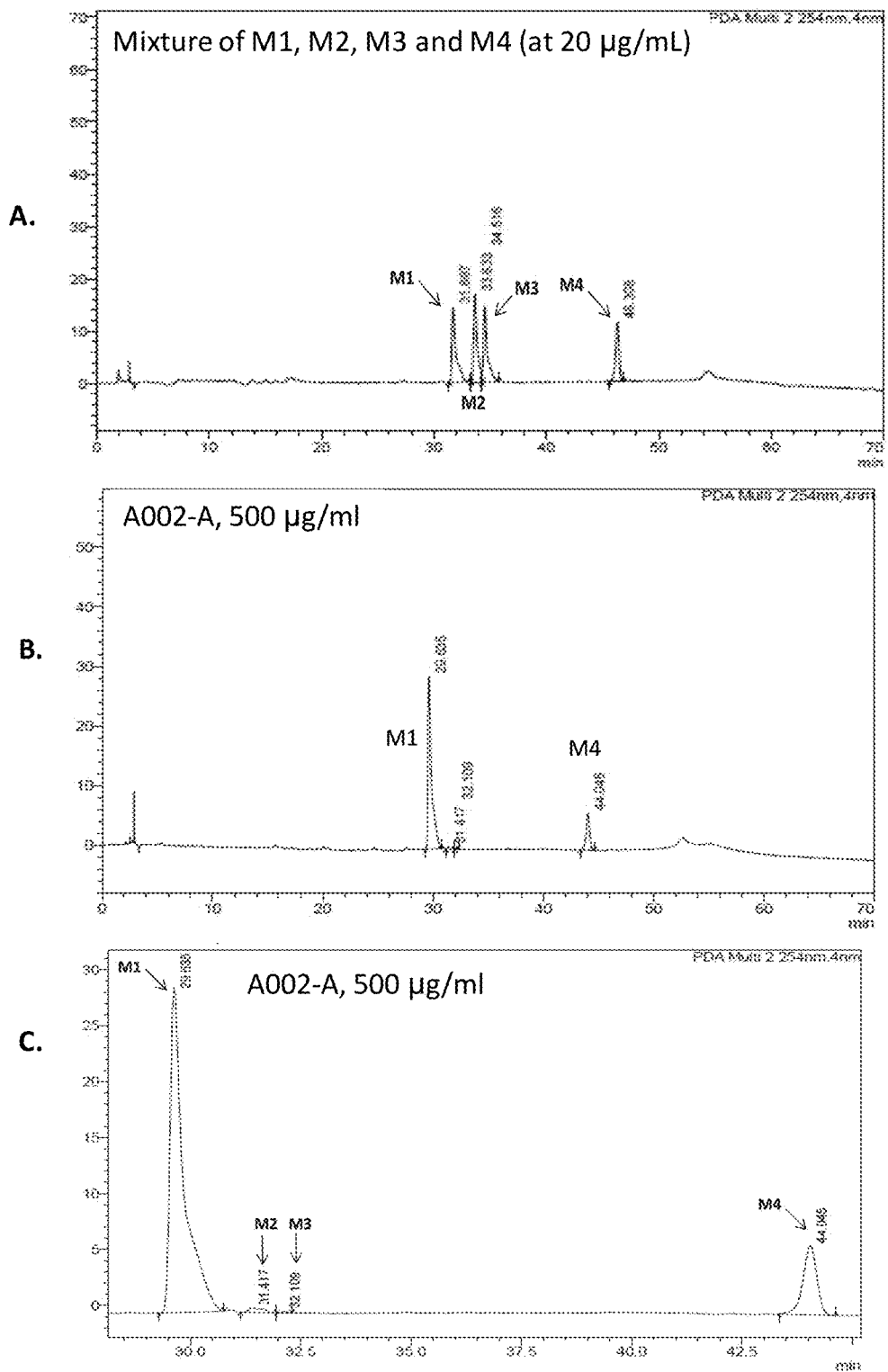
FIG. 1 shows the HPLC chromatogram of rohitukine-rich *Dysoxylum binectariferum* extract A002-A, showing four marker compounds in the extract. Labels of each peak indicate the retention time [M1=rohitukine, M2=Chrotacumine K; M3=rohitukine N-oxide; M4=Schumaniofioside A].

SR-A002-AEF indicates the sustained release formulation of rohitukine-enriched extract of *D. binectariferum*; SR-A002-B indicates the sustained release formulation of hydroalcoholic extract of *D. binectariferum*; A002-A and A002-B are hydroalcoholic extracts of *D. binectariferum*; A002-AEF is rohitukine-enriched fraction of *D. binectariferum*; CIA, collagen induced arthritis; EC, ethyl cellulose; HPLC, high-performance liquid chromatography; HPMC-K15M, hydroxypropyl methyl cellulose-K15M; PVP-K30, polyvinylpyrrolidone K 30; HEC, hydroxy ethyl cellulose; TNF-alpha, tumor necrosis factor-alpha; IL-6, interleukin-6; LPS, lipopolysaccharide; PDA, photo-diode array.

DETAILED DESCRIPTION OF THE INVENTION

The present invention provides novel sustained release formulations of rohitukine-rich *Dysoxylum binectariferum* extract or fraction for the treatment of inflammatory diseases involving elevated levels of proinflammatory cytokines. More specifically, this invention is further directed to methods of preparation of rohitukine-rich *Dysoxylum binectariferum* extract or fraction from the leaves of the plant using ethanol and water in ratio of 1:1. The novel formulations developed herein, apart from its key advantage of sustained release profile, are free flowing powders and easy to fill into the capsules.

The oral sustained release formulation according to one exemplary embodiment of the present invention comprises rohitukine-rich extract of leaves of *Dysoxylum binectariferum* (Family: Meliaceae). The "rohitukine-rich extract of *Dysoxylum binectariferum*" is characterized for the content of rohitukine ($C_{16}H_{19}NO_5$, molecular weight=305.33), and schumaniofioside A ($C_{16}H_{18}O_9$, molecular weight=354.15) which should be at least 2% w/w and 1% w/w, respectively.

Rohitukine

Schumaniofioside A

In this case, a mixture of water and ethanol (preferably in the ratio of 50:50) may be used as the extraction solvent. The extract is prepared in the form of dried lyophilized powder by extracting the leaves of *Dysoxylum binectariferum* with water and ethanol by mechanical stirring at room temperature (20-30° C.), filtering the extract, followed by concentrating the extract under reduced pressure. The enrichment of the extract for rohitukine content, if required, can be done by further extracting the above extract with methanol-acetone (1:1) solvent.

There is provided a novel drug delivery composition for the controlled release of an active ingredient in the gastrointestinal tract over a prolonged period of time. In particular, there is provided a novel sustained release oral formulations of *Dysoxylum binectariferum* for supplying optimum plasma concentrations of the biologically active compound "rohitukine". These novel formulations are hydrophilic matrix based delivery systems which usually work by diffusion rate control mechanism. These dosage forms is selected from the group consisting of a matrix tablet or a hard gelatin two piece capsule filled with polymeric granules or microparticles of granulated extract which prolong the release of rohitukine from the matrix, resulting in its controlled systemic exposure.

During the investigations, it was observed that the content of rohitukine varies with the age of leaves. The young leaves of *Dysoxylum binectariferum* contain less percentage of rohitukine in comparison to old and mature leaves. Young leaves contain ~1.5-3% w/w of rohitukine whereas old leaves contain 5-7% w/w rohitukine. Therefore, in order to have a standardized "rohitukine-rich *Dysoxylum binectariferum* extract" to be used for formulation development, it can be prepared from leaves of any age; however the final extract prepared should have at least 2% w/w of rohitukine and 1% of schumaniofioside A. If the % rohitukine content of prepared hydroalcoholic extract is in between 4-8%, it can be directly used for formulation/product development without requirement of any further enrichment. However, if the % rohitukine content of hydroalcoholic extract is between 2-4%, then the enrichment is required. The hydroalcoholic extracts containing less than 2% of rohitukine are to be discarded. The enrichment protocol described herein, generally results in doubling the rohitukine content. The enrichment protocol involves dissolving the hydroalcoholic extract in 50:50 v/v methanol:acetone. The methanol:acetone soluble fraction contains 50% enriched rohitukine content. Like rohitukine, the % content of schumaniofioside A also gets doubled during enrichment process.

Two hydroalcoholic extracts (A002-A and A002-B) prepared from leaves collected at two different times, and possibly of varied age of leaves were analyzed by HPLC for rohitukine and schumaniofioside A content. The hydroalcoholic extract A002-A was found to contain 2.64% w/w of rohitukine and 5.15% w/w of schumaniofioside A. This extract was further subjected for enrichment of rohitukine content. The acetone:methanol soluble fraction (enriched fraction-A002-AEF) contains 5.1% w/w of rohitukine and 9.74% w/w of schumaniofioside A. The hydroalcoholic extract A002-B was found to contain 6.62% w/w of rohitukine and 2.32% w/w of schumaniofioside A. This extract was directly used for formulation development without need of any enrichment. Thus, A002-AEF and A002-B which contain 5.1 and 6.62% of rohitukine, falling in the prescribed range of rohitukine content.

Particularly, this invention provides the method for preparation of novel sustained release formulations wherein the extract or fraction is wet-granulated using excipients, biodegradable polymers and/or non-biodegradable polymers alone or in combination, and the said granules are either filled into a capsule or compressed into a tablet. The said formulation comprising a granulated extract or fraction of *Dysoxylum binectariferum* with polymers results in sustained release of the extract or fraction in the gastrointestinal tract.

Moreover, this invention provides formulations wherein the total in-vitro dissolution time of said formulations required for release of 100% of the active ingredients is in the range of 16 to 24 hours, as determined by the U.S.P. dissolution apparatus by Basket method at a speed of 50 rpm, and temperature of 37° C.±0.5, using 900 ml of dissolution media (pH 1.2 buffer for first 2 h and phosphate buffer pH 6.8 up to 24 h).

The significant inhibition of proinflammatory cytokine TNF-alpha in human monocytic THP-1 cells by rohitukine-rich *Dysoxylum binectariferum* extract A002-AEF (rohitukine content=5.1% w/w) and *Dysoxylum binectariferum* hydroalcoholic extract A002-A (rohitukine content=2.6% w/w) is depicted in FIG. 3A. The LPS induced release of TNF-alpha was significantly suppressed by both extracts at the test concentrations (1.56-12.5 µg/ml).

In in-vivo efficacy studies, the rohitukine-enriched fraction (A002-AEF) was found to be superior over hydroalcoholic extract (A002-A). A002-AEF at 200 mg/kg has suppressed the levels of TNF-alpha in both LPS-induced septic shock model (BALB/c mice) as well as in collagen induced arthritis model (DBA/1J mice).

The spectrums of conditions for which the inventive extract can be used includes, but not limited to rheumatoid arthritis, cystic fibrosis, atherosclerosis and cancer.

The following examples are given by way of illustration of the working of the invention in actual practice and should not be construed to limit the scope of the present invention in any way.

Example 1. Preparation of Rohitukine-Rich *Dysoxylum binectariferum* Extracts/Fraction: A002-AEF and A002-B The authentic plant material *Dysoxylum binectariferum* (leaves) was collected by the Plant Biotechnology Division of Indian Institute of Integrative Medicine (CSIR), Jammu, in December 2016 from Forest Research Institute, Dehradun (Uttarakhand) (coordinates of the location are: Latitude DMS: 30° 20'37.57"N; Longitude DMS: 77° 59'58.41"E). Plant was identified and authenticated at IIIM and herbarium sheet was prepared and submitted to Janaki Ammal herbarium, IIIM (Acronym RRLH, accession no. 22163). Dried samples of leaves were submitted to the institutional crude drug repository (accession no. 3892). The dried and powdered plant material (500 g) was extracted with a water/ethanol solution of 50% ethanol by volume and then freeze dried. The steps involved in the preparation of extract are as follows:

1. Mixing the powdered plant drug with an extracting hydro-alcoholic solution in the proportion of 1:1 (m/m), using ethanol as alcohol, in the initial proportion of 1 part plant ingredient to 5-10 parts of hydroalcoholic solution, based on the mass of the materials. Performing the extraction of the compounds for a period of at least 3 hours at a room temperature in a closed reactor under mechanical stirring.
2. Filtering the mixture obtained in step 1, in order to obtain a first intermediary hydro-alcoholic extract and a first residue consisting of the components of the non-extracted plant drug.
3. Mixing the first residue consisting of the components of the non-extracted plant drug with a fresh extracting hydroalcoholic solution, constituted of a mixture of ethanol and water in 1:1 v/v ratio. The volume of hydro-alcoholic solution to be added is two-third of the volume of the first extracting hydro-alcoholic solution added in step 1. The extraction was performed for a period of 3 hours at a room temperature in a closed reactor under mechanical stirring.
4. Filtering the mixture obtained in step 3, in order to obtain a second intermediary hydro-alcoholic extract and a second residue constituted of the components of the non-extracted plant drug.
5. Treating the second residue as per steps 3 and 4.
6. Evaporation of the solvent from combined hydroalcoholic filtrate by vacuum assisted evaporation (temperature of 40° C., vacuum of 250 mm Hg) until the mass corresponds to approximately 25% of the mass of the mixture obtained.
7. Finally, freeze-drying of the remaining extract to get free-flowing powdered extract A002-A (extractive value=18-25%). The hydroalcoholic extract A002-B was also obtained using similar procedure (steps 1-7), using another batch of plant material.

The extract A002-A as obtained in step 7 was found to contain 2.64% w/w of rohitukine. This extract was subjected for rohitukine-enrichment, as described below (steps 8-12):
8. The hydro-alcoholic extract A002-A as obtained above in step 7, was dissolved in 50:50 v/v methanol:acetone (10 ml/g) and the mixture was stirred for 3 h.
9. Filtering the mixture obtained in step 8 to get first enriched fraction and first residual component of hydroalcoholic extract which still contains rohitukine.
10. Mixing the first residue of hydro-alcoholic extract and fresh solvent mixture containing 50:50 v/v methanol: acetone (10 ml/g) and mixture was stirred for 3 h.
11. Filter the mixture obtained in step 10 to obtain second enriched fraction.
12. The methanol:acetone soluble portion obtained from steps 8 and 11 were mixed and concentrated over vacuo rotavapor to get dried powder of active ingredient (rohitukine) enriched fraction. The extractive value of rohitukine-enriched fraction (A002-AEF) from powdered plant material (on dry weight basis) is found to be 9-12% w/w. This enriched fraction was found to contain 5.1% w/w of rohitukine.

The authentic plant material *Dysoxylum binectariferum* (leaves) collected at different time than above was processed for preparation of hydroalcoholic extract using steps 1-7 as described above. The extract obtained A002-B was found to contain 6.62% of rohitukine. This extract was directly used for formulation development.

The standardization of the extract/enriched fraction was done by HPLC method using four chemical markers namely rohitukine, rohitukine-N-oxide, chrotacumine K, and schumaniofioside A. The % content of four markers was determined as follows. Briefly, the stock solution (1000 µg/mL) of rohitukine (M1), chrotacumin-K (M2), rohitukine-N-oxide (M3) and schumaniofioside A (M4) were prepared in MeOH. The simultaneous estimation of markers in IIIM-64 was performed using RP-Amide column (Ascentis®, 5 µm, 25 cm×4 mm) using PDA detector (SPD-M20A, Prominence, Shimadzu). Calibration curve for each marker was prepared in the concentration range of 0, 2.5, 5, 10, 20, 40 and 80 µg/mL. For simultaneous estimation of markers in extracts/fractions, the ~5 mg of extract/fraction was transferred in an eppendorf tube containing 1 mL of MeOH, and the mixture was sonicated. Eppendorf tubes were centrifuged at 16000 RCF (G-force) for 10 min to separate solid matrix, if any. The supernatant was injected into the HPLC system after diluting it with MeOH to get concentration of 500 µg/mL. The % content of each marker was calculated using a regression equation obtained from the calibration curve of each reference standard of a marker. HPLC method and conditions were as follows.

HPLC column: RP-Amide column (Ascentis®, 5 µm, 25 cm×4 mm)
Mobile phase: A: 0.1% v/v Formic acid and B: MeOH
Injection volume: 5.0 µL (SIL-20A HT Prominence autosampler)
Flow rate: 1.0 ml/min (pump, Shimadzu LC-6AD)
Column oven temperature: 37° C. (column oven, CTO-10ASVP)
Detection: 254 nm using Diode array (SPD-M20A, Prominence, Shimadzu)
Run time: 70 min
HPLC method: Gradient elution (5% B for 0-5 min, 5-25% B for 5-35 min, 25% B for 35-40 min, 25-35% B for 40-50 min, 35-5% B for 50-65 min and 5% B for 65-70 min.

In general, the hydro-alcoholic extract comprises rohitukine (marker M1) as the major component (2.6-7.8% w/w of rohitukine in hydroalcoholic extract). Enrichment of this extract using methanol:acetone solvent resulted in doubling the rohitukine content; the obtained enriched fraction contain 5-13% w/w of rohitukine. Marker M2 (chrotacumine K) and M3 (rohitukine-N-oxide) were present in minor quantities and their content ranged from 0.01-0.71% w/w; however the fourth marker schumaniofioside A (M4) was also present in good quantity (0.55-5% w/w in hydroalcoholic extract; and 4-10% in enriched fraction). The quantification results are shown in Table 1.

TABLE 1

Marker contents in hydroalcoholic extracts IIIM-64-A002 and enriched fractions IIIM-64-REF

| | | % Content of marker compound in the extract/fraction (Mean ± SD)* | | | | | |
|---|---|---|---|---|---|---|---|
| | | Hydroalcoholic extracts IIIM-64-A002 | | | | Enriched fractions IIIM-64-REF | |
| Marker compound | Retention time (min) | VKB-2 | VKB-4 | VKB-6 (A002-B) | VKB-7 (A002-A) | VKB-6EF (A002-BEF) | VKB-7EF (A002-AEF) |
| Rohitukine (M1) | 31 | 5.64 ± 0.254 | 7.76 ± 0.629 | 6.62 ± 0.453 | 2.64 ± 0.159 | 13.25 ± 0.835 | 5.1 ± 0.259 |
| Chrotacumine K (M2) | 33 | 0.006 ± 0.004 | 0.17 ± 0.021 | 0.1 ± 0.01 | 0.017 ± 0.003 | 0.03 ± 0.003 | 0.031 ± 0.003 |
| Rohitukine-N-oxide (M3) | 34 | 0.71 ± 0.033 | 0.045 ± 0.006 | 0.018 ± 0.004 | 0.011 ± 0.001 | 0.49 ± 0.031 | 0.015 ± 0.004 |
| Schumaniofioside A (M4) | 46 | 0.55 ± 0.014 | 2.55 ± 0.204 | 2.32 ± 0.157 | 5.15 ± 0.31 | 4.77 ± 0.335 | 9.74 ± 0.382 |

*Average of three determinations. Enriched fractions "VKB-6EF" and "VKB-7EF" were prepared from their corresponding hydroalcoholic extracts "VKB-6" and "VKB-7"

Example 2. pH Dependent Stability of Rohitukine

The stability of rohitukine was performed in pH 1.2 buffer, pH 4.0 buffer, phosphate buffer pH 6.8, phosphate buffered saline pH 7.4, SGF (pH 1.2), SIF (pH 6.8) and plasma up to 24 hrs. The % of rohitukine hydrolyzed was determined by HPLC analysis. The HPLC analysis was carried out using the method as described in example 1. Results of stability studies indicated that rohitukine is stable at all the conditions tested.

Example 3. Preparation of Novel Sustained Release Formulations

The rohitukine-rich *Dysoxylum binectariferum* extract/fractions A002-AEF or A002-B and excipient(s) were weighed accurately and mixed thoroughly using mortar and pestle. This mixture was kneaded using 10% PVP-K30 solution in isopropanol (as a binder) to form a dough. This dough was then passed through sieve #10. The obtained granules were dried in oven at 50° C. for 30-60 min. The dried granules were passed through sieve #10 and retained on sieve #30. The dried granules were stored in air-tight container in vacuum desiccator till further analysis. The formulations were assayed for rohitukine content using HPLC method as mentioned in example 1. Based on the results of assay, formulation equivalent to 10 mg of rohitukine was filled into the hard gelatin capsules of size '0'. These capsules were analyzed for in-vitro dissolution profile. The composition and % release of rohitukine of SR formulations are provided in Table 2.

SR-A002-B were studied using USP dissolution apparatus as per the protocol given in USP 2011 (The United States Pharmacopoeial Convention. 2011, Pages 1-8). Lab-India Dissolution Tester (Model: DS 8000; apparatus 1—Basket Apparatus) was used for this study. Various parameters are: RPM=50; Temp.=37° C.±0.5; Volume of dissolution medium=900 ml; Dissolution medium=hydrochloric acid buffer (pH 1.2) for first 2 h followed by phosphate buffer (pH 6.8) up to 24 h, sampling time points (h)=0.5, 1, 2, 4, 8, 12, 16, 20 and 24.

Figure 2:
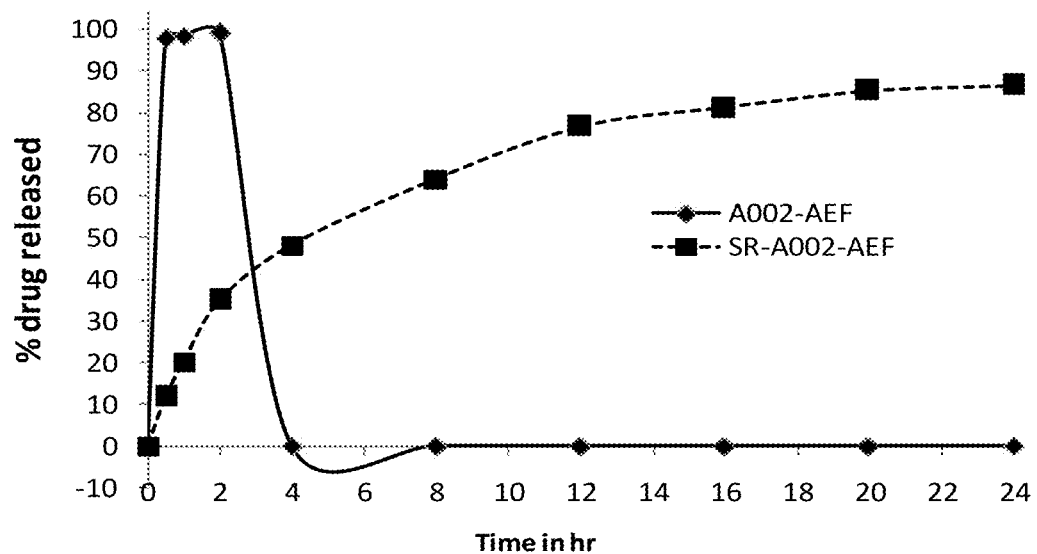
FIG. 2 shows the in-vitro dissolution profiles of developed sustained release formulations SR-A002-AEF (A) and SR-A002-B (B) along with their plain extracts/fractions. In this study, the % release of rohitukine was determined by HPLC analysis (SR-A002-AEF indicates the sustained release formulation of rohitukine-enriched fraction of *D. binectariferum*; and SR-A002-B indicates the sustained release formulation of hydroalcoholic extract of *D. binectariferum*.
Figure 2:
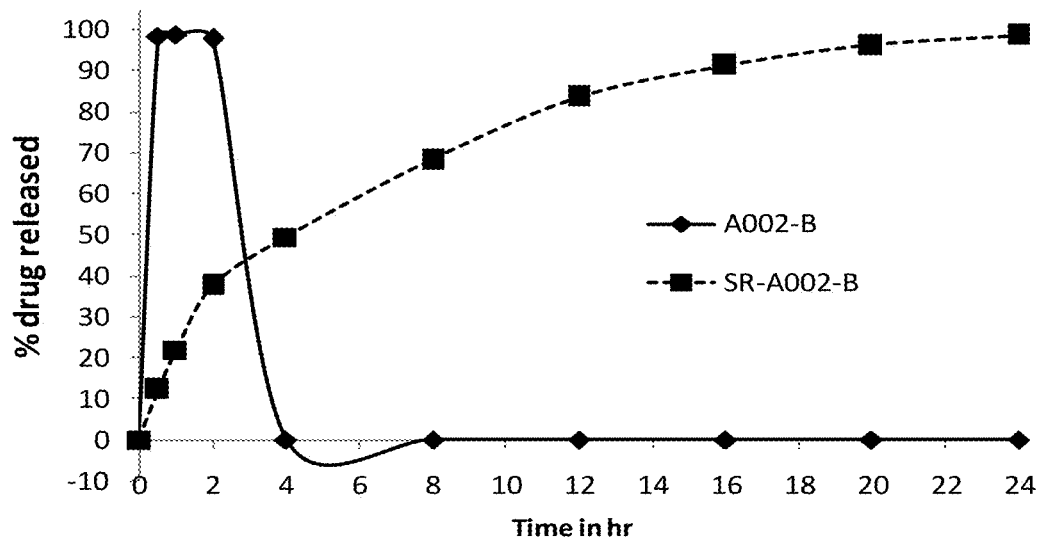

The percent release of rohitukine from formulations was determined by HPLC analysis. Results showed that the plain rohitukine-rich *Dysoxylum binectariferum* extracts A002-AEF and A002-B showed 100% release of rohitukine in 30 min and rohitukine was not detected after 2 h in new buffer (phosphate buffer pH 6.8), whereas the SR formulations SR-A002-AEF and SR-A002-B showed only 13% release of rohitukine after 30 min, 56% in 4 h, 75% in 8 h, 94% in 16 h and 99% after 24 h. The composition of representative formulation batches are given in Table 2. The optimized SR formulations SR-A002-AEF and SR-A002-B comprise the use of rohitukine rich *Dysoxylum binectariferum* extract or fraction, HPMC-K15M and sodium alginate in 50:40:10 w/w ratio. The dissolution profile of optimized SR formulations SR-A002-AEF and SR-A002-B are shown in FIG. 2A. These batches were considered as the optimum batches with sustained release profile over a period of 24 h.

The summarized overview of optimized formulations with their $T_{10\%}$, $T_{50\%}$ and $T_{75\%}$ values are shown in Table 3.

TABLE 2

Composition of sustained release formulations SR-A002-AEF and SR-A002-B, the % release of rohitukine during dissolution study and intactness of formulations

| Sr No | Formulation code | Composition of the formulation[a] | Drug: Polymer ratio | Intact matrix form after 24 h | % release of rohitukine after 0.5 h | 16 h | 24 h |
|---|---|---|---|---|---|---|---|
| 1 | A002-AEF (plain rohitukine-rich *Dysoxylum binectariferum* extract filled in capsules) | A002-AEF | NA | No | 98.6 | 0 | 0 |
| 2 | SR-A002-AEF | A002-AEF: 1 g HPMC-K15M: 0.8 g Sodium alginate: 0.2 g | 50:50 | yes | 13.2 | 94.3 | 98.5 |
| 3 | A002-B (plain rohitukine-rich *Dysoxylum binectariferum* extract filled in capsules) | A002-B | NA | No | 98.0 | 0 | 0 |
| 4 | SR-A002-B | A002-B: 1 g HPMC-K15M: 0.8 g Sodium-alginate: 0.2 g | 50:50 | Yes | 15.9 | 88.1 | 100 |

[a]10% PVP-K30 solution in isopropanol was added as a binder in each formulation to form a dough.

Example 4. Dissolution Profile of Sustained Release Formulations

The dissolution profile of capsules filled with rohitukine-rich *Dysoxylum binectariferum* extracts A002-AEF and A002-B and their SR formulations SR-A002-AEF and The release half-life ($T_{50\%}$) for rohitukine in plain extracts is less than 0.5 h, whereas it is 4 h in SR formulations SR-A002-AEF and SR-A002-B. The $T_{75\%}$ (time taken to release 75% of drug from the formulation) for rohitukine in plain extract is less than 0.5 h, whereas it is 8 and 10 h in SR formulations SR-A002-AEF and SR-A002-B.

TABLE 3

Dissolution release profile of rohitukine in optimized formulations of *Dysoxylum binectariferum*

| Extract and its formulations | $t_{10\%}$ (hr) | $t_{50\%}$ (hr) | $t_{75\%}$ (hr) |
|---|---|---|---|
| A002-AEF (plain extract) | — | — | <0.5 |
| SR-A002-AEF (SR formulation of A002-AEF) | <0.5 | ~4.0 | ~8.0 |
| A002-B (plain extract) | — | — | <0.5 |
| SR-A002-B (SR formulation of A002-B) | <0.5 | ~4.0 | ~10.0 |

$t_{10\%}$ = time taken to release 10% of drug from the formulation; $t_{50\%}$ = dissolution half-life; $t_{75\%}$ = time taken to release 75% of drug from the formulation.

Example 5. In-Vitro Cytokine Inhibition in THP-1 Cells

Figure 3:
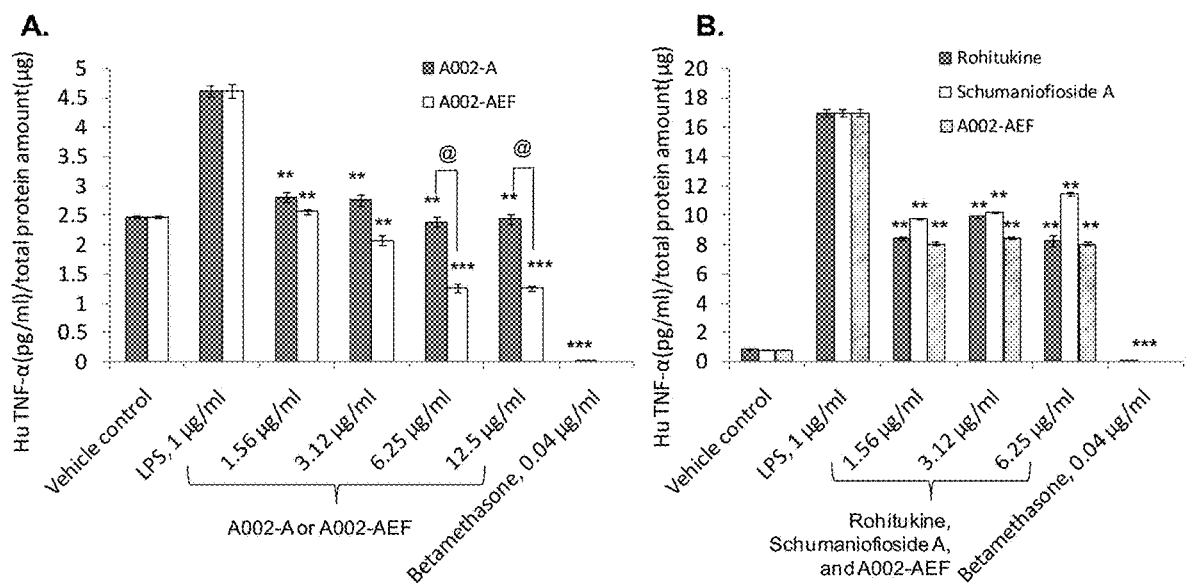
FIG. 3 The in-vitro effect of hydroalcoholic extract (A002-A), its enriched fraction (A002-AEF), two major marker compounds rohitukine and schumaniofioside A on the production of TNF-alpha in THP-1 cells. Statistical analysis was performed by ANNOVA test by comparing the LPS-treated group with test-item treated groups.  p<0.005; * p<0.001. The comparison was also made between A002-A and A002-AEF. The results with p value <0.05 (@) were considered significant.

For the in vitro analysis of pro-inflammatory cytokine (TNF-α), human leukemia THP-1 cells were seeded in a 24-well plate at a density of 4×10$^5$ cells/ml of RPMI medium per well. THP-1 cells were then treated with PMA (20 ng/ml) for differentiation into macrophages for 18 h followed by a rest period of 48 h. Cells were further co-treated with test samples and 1 μg/ml of lipopolysaccharide (LPS) in a serum-free medium. Culture supernatant was harvested after 24 h for analysis of TNF-α by using OptEIA ELISA Kits from BD Biosciences. Total protein content for all the samples was calculated by using Bradford reagent from Bio-Rad Laboratories. All samples were normalized by dividing cytokine concentration with total quantity of protein. Results are shown in FIG. 3. Betamethasone was used as positive control in this study.

The results presented in FIG. 3A shows the comparative effect of hydroalcoholic extract (A002-A) and its rohitukine-enriched fraction (A002-AEF) on the production of TNF-alpha in THP-1 cells. It was observed that both A002-A and A002-AEF showed suppression of LPS-induced TNF-alpha levels at all four tested concentrations (1.56, 3.12, 6.25 and 12.5 μg/mL). The enriched fraction (A002-AEF) was found to be superior over hydroalcoholic extract (A002-A) at all tested concentrations. Two major marker compounds (rohitukine and schumaniofioside A) of extract/fraction were also tested for inhibition of LPS-stimulated TNF-alpha levels in THP-1 cells (FIG. 3B). Both marker compounds displayed significant inhibition of TNF-alpha at all three tested concentrations (1.56, 3.12, and 6.25 μg/mL). The TNF-alpha inhibition effect of both marker compounds and the enriched fraction was found to be similar. The corresponding rohitukine and schumaniofioside A content in enriched fraction at its three tested doses 1.56, 3.12, and 6.25 μg/mL would range between 0.08-0.32 μg/mL and 0.15-0.61 μg/mL, respectively. Thus, the significant cytokine inhibition effect obtained in enriched fraction, which was similar to the 1.56-6.25 μg/mL doses of rohitukine and schumaniofioside A, accounts to the "synergistic behavior" of these two natural products as well as other compounds in the extract/fraction.

Example 6. Comparative Oral Pharmacokinetic Study of Plain Extract ((Rohitukine-Enriched Fraction of *Dysoxylum binectariferum*) Versus its SR Formulation "SR-A002-AEF" in SD Rats The pharmacokinetic study was performed in male SD rats. First the pharmacokinetic study of "rohitukine" was performed by both intravenous as well as per oral (PO) routes in order to understand the oral exposure and oral bioavailability of rohitukine. Rohitukine was administered at 5 mg/kg by IV route and at 50 mg/kg by oral route. For comparative oral pharmacokinetic study of plain extract (A002-AEF) and SR formulation "SR-A002-AEF" formulation (filled in 9e1 capsules), the dose equivalent to 6.77 mg/kg dose of rohitukine was administered in SD rats in both these groups. Blood samples were collected (n=3/time point) at 0.083 (IV only), 0.25, 0.5, 1, 2, 4, 8 and 24 h, post-dose. At each time point about 200 μL of blood was collected by jugular vein into a labeled microfuge tube containing 200 mM K2EDTA solution (20 μL per mL of blood) and equivalent volume of heparinized saline was replaced following sample collection. The blood samples were processed to obtain the plasma samples within 30 min of scheduled sampling time. All plasma samples were stored below −60° C. until bioanalysis. The plasma samples were analyzed for rohitukine content using a fit-for purpose LC-MS/MS method with a lower limit of quantification (LLOQ) of 9.95 ng/mL. The pharmacokinetic parameters of rohitukine were calculated using the non-compartmental analysis tool of validated Phoenix® WinNonlin® software (version 6.3). Results are shown in FIG. 4A-D.

Following a single intravenous bolus administration of "rohitukine" to male Sprague Dawley rats (5 mg/kg), the mean plasma clearance (Cl) was found to be high (72.7 mL/min/kg which is almost 1.32-folds higher than the normal hepatic blood flow of 55 mL/min/kg in rats) with elimination half-life ($t_{1/2}$) of 0.382 h. The volume of distribution at steady state was found to be 1.69 L/kg which is almost 2.41-fold higher than the normal total body water content (0.7 L/kg in rats). Mean plasma exposure ($AUC_{last}$) was found to be 1130 h*ng/mL.

Following a single oral gavage administration of "rohitukine" to male Sprague Dawley rats (50 mg/kg), median time to reach the maximum plasma concentration was found to be 0.25 h with peak plasma concentration ($C_{max}$) of 14900 ng/mL. Plasma exposure ($AUC_{last}$) was found to be 26400 h*ng/mL. The terminal plasma half-life was found to be 1.06 h. The absolute oral bioavailability of "rohitukine" was determined to be >100% (FIG. 4A-B).

Figure 4:
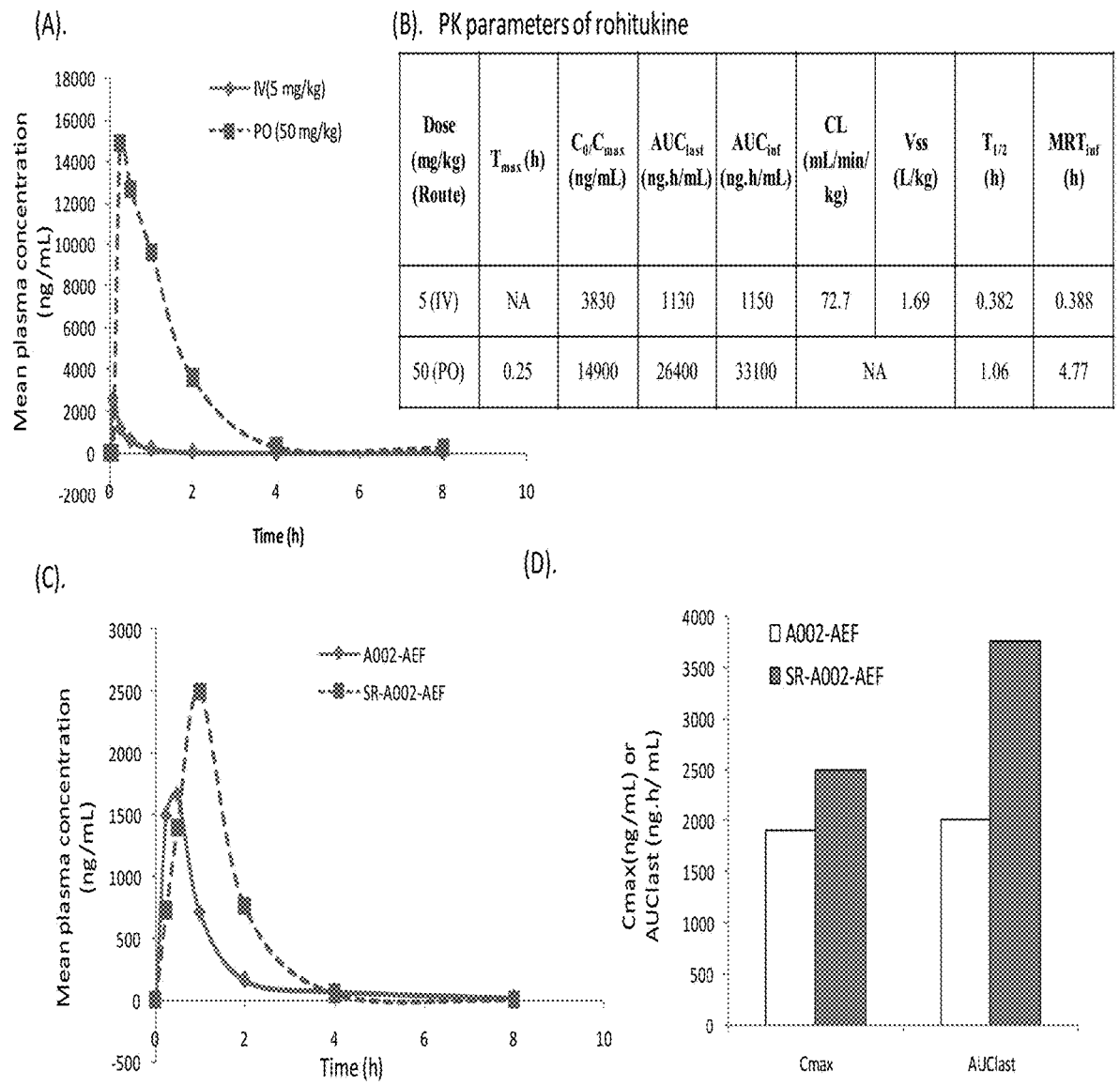
FIG. 4 The pharmacokinetic analysis of rohitukine, A002-AEF (rohitukine-enriched fraction of *Dysoxylum binectariferum*) and SR-A002-AEF (sustained release formulation of A002-AEF) in SD rats. (A). The plasma concentration versus time curve for rohitukine after administration by IV and PO route. (B). PK parameters of rohitukine; (C). The comparative plasma concentration versus time curve for A002-AEF and SR-A002-AEF after administration by PO route, at a dose equivalent to 6.77 mg/kg dose of rohitukine. (D). Comparison of $C_{max}$ and $AUC_{last}$ of plain extract (A002-AEF) and SR formulation (SR-A002-AEF).

Next, the comparative oral pharmacokinetic analysis of plain extract A002-AEF and its SR formulation SR-A002-AEF was performed in SD rats (FIG. 4C-D). The extract/formulation equivalent to 6.77 mg/kg of rohitukine were filled in the 9e1 capsules, which were delivered to rats by oral route. The PK results indicated that there is 2-fold increase in the $AUC_{last}$ of rohitukine in case of SR formulation in comparison to that of plain extract. Similarly, the $T_{max}$ value was doubled in SR formulation in comparison to plain extract. The time-plasma concentration curve of extract and formulation is depicted in FIG. 3C. The comparative PK results clearly indicate that there is significant increase in the oral exposure of "rohitukine" in case of SR formulation in comparison to plain extract (AUC increased from 2010 to 3750 ng·h/mL). The improvement in oral PK profile directly correlates with its oral in-vivo efficacy.

Example 7. In-Vivo Effect of Rohitukine, Hydroalcoholic Extract (A002-A) and Rohitukine-Enriched Fraction (A002-AEF) on TNF-α Production in LPS Induced Septic Shock Model in BALB/C Mice The effect of rohitukine, hydroalcoholic extract (A002-A) and rohitukine-enriched fraction (A002-AEF) on TNF-α secretion was studied in LPS induced septic shock model in BALB/C mice. BALB/C female mice (20-25 g) were randomly divided into 6 groups (n=4 per group). Animals were treated according to the following pattern: group 1 (vehicle), group 2 (LPS, 20 mg/kg), group 3 (Rohitukine, 20 mg/kg), group 4 (A002-A, 200 mg/kg), group 5 (A002-AEF, 200 mg/kg), group 6 (dexamethasone, 10 mg/kg). The hydroalcholic extract (A002-A) and its enriched fraction A002-AEF was dissolved in water and dexamethasone was dissolved in PBS. PBS/water was used as a vehicle control. Compounds and vehicle were administered perorally for 1 h prior to treatment with LPS. LPS was injected through intraperitoneal route for 5 h. Blood was collected and serum was extracted for performing ELISA analysis of TNF-α cytokine. The ELISA was performed according to manufacturer's instructions (BD Bioscience). The absorbance was measured at 450 nm and each estimated cytokine value was normalized with total serum protein.

Figure 5:
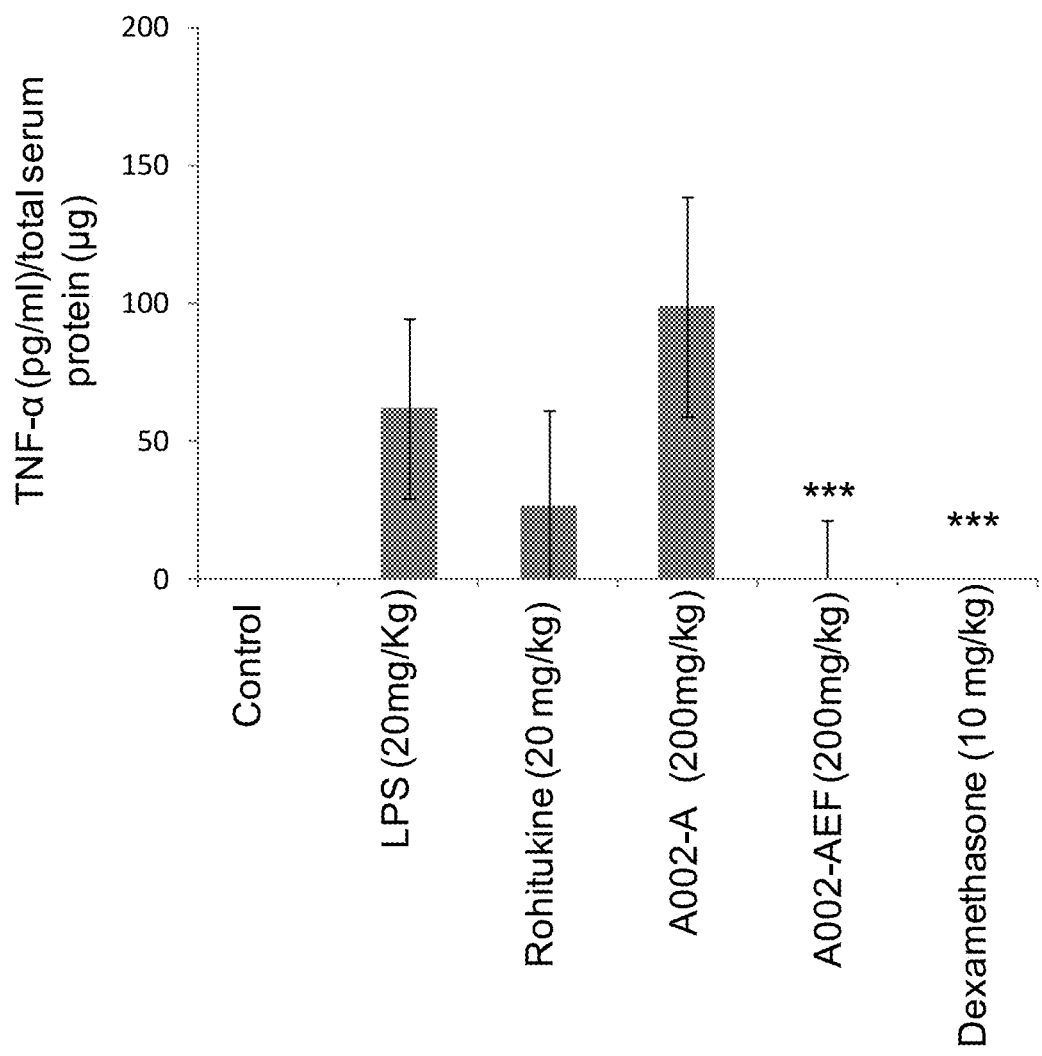
FIG. 5 In-vivo effect of rohitukine, A002-A and A002-AEF on the production of TNF-alpha in LPS induced Septic Shock Model in BALB/C mice (A002-A: hydroalcoholic extract of *Dysoxylum binectariferum* leaves; A002-AEF: rohitukine-enriched fraction of *Dysoxylum binectariferum* leaves). Statistical analysis was performed by ANNOVA test by comparing the LPS-treated group with test-item treated groups. *** p<0.001.

Results of this study are shown in FIG. 5. It was observed that hydroalcoholic extract (A002-A) at 200 mg/kg does not led to decrease in the levels of TNF-alpha; however the enriched fraction (A002-AEF) at the same dose has resulted in complete reduction in TNF-alpha levels. The results of this study has clearly indicated the benefit of rohitukine-enrichment in the extract.

The natural product 'rohitukine' at 20 mg/kg (PO) dose was not able to significantly inhibit the serum TNF-alpha levels; however enriched fraction A002-AEF (which contains 5% w/w rohitukine) at 200 mg/kg dose (which corresponds to 10 mg/kg dose of rohitukine) displayed statistically significant inhibition of serum TNF-alpha. The possible reason for this effect is because of the presence of another natural product ' schumaniofioside A' (9.7% w/w) in the enriched fraction which also has its own inhibitory effect on proinflammatory cytokine TNF-alpha. In case of enriched fraction, the "synergistic effect" of rohitukine, schumaniofioside A along with other natural products plays crucial role in its efficacy in this in-vivo model (FIG. 5).

Example 8. Effect of Rohitukine, Hydroalcoholic Extract and Enriched Fraction in Collagen Induced Arthritis Model in DBA/1J Mice Six weeks old DBA/1J mice (procured from Jackson Laboratories, USA) were used in this study. On the day of the immunization (day 1), required amount of Chicken collagen II (CII), 2 mg/ml (Chondrex Inc, USA) stock solution was thawed at 4° C. into a small (20 ml) glass bottle. Equal volume of CII solution was added to the complete Freund's adjuvant (CFA), 1 mg/ml, (Sigma aldrich, USA) in 1:1 ratio and homogenized at 4° C. to produce a homogenous, stiff, white creamy emulsion for immunization. Mice were weighed and anesthetized with isoflurane. 150 μl of CII/CFA (1:1) emulsion was injected intradermally at two different sites into the mice lower back (previously shaven) on day 1. Mice were given the booster on day-21 in a similar manner as day 1 except that CII was emulsified in incomplete Freund's adjuvant. Mice were given booster of LPS from *E. coli* (50 μg/mouse; Sigma Aldrich, USA) on day 28. Dosing of the test samples in DBA/1J mouse CIA model was initiated after development of clinical symptoms. Animals were randomized into different treatment groups based on clinical scores on day 33. Treatment continued from day 34 to day 48. Serum IL-6, TNF-α estimation was done using ELISA kit from R & D Systems, USA. All values are expressed as Mean±SEM. * $p<0.05$ as compared to vehicle treatment, one way ANOVA followed by Dunnett's multiple comparison test.

Figure 6:
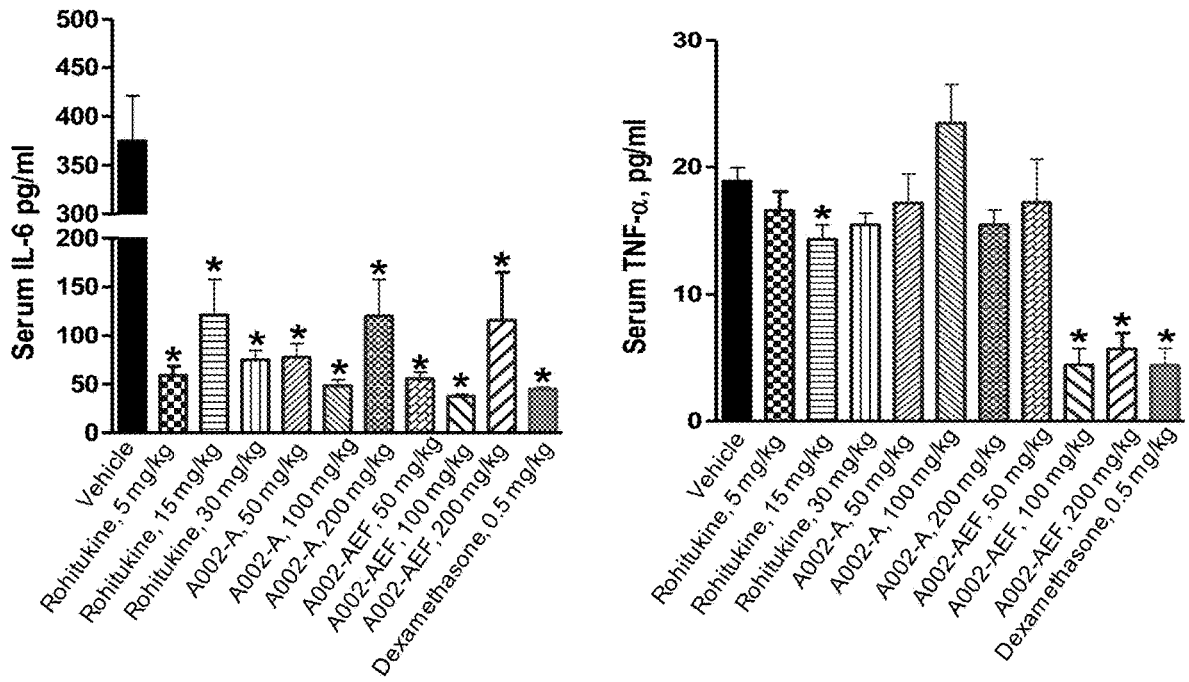
FIG. 6 In-vivo effect of rohitukine, A002-A and A002-AEF on the production of TNF-alpha and IL-6 in collagen-induced arthritis (CIA) model in DBA/1J mice (A002-A: hydroalcoholic extract of *Dysoxylum binectariferum* leaves; A002-AEF: rohitukine-enriched fraction of *Dysoxylum binectariferum* leaves). All values are expressed as Mean±SEM. The statistical analysis was performed by comparing the treatment groups with vehicle control (* p<0.05) using one way ANOVA followed by Dunnett's multiple comparison test.

The results of this study has indicated that the oral administration of rohitukine, hydroalcoholic extract (A002-A) as well as rohitukine-enriched fraction (A002-AEF) in arthritic mice resulted in decreased levels of serum IL-6 cytokine. However, there was no significant inhibition of TNF-alpha cytokine in case of rohitukine at 5-30 mg/kg doses. Similarly, in case of hydroalcoholic extract (A002-A), there was no inhibitory effect on the levels of TNF-alpha at any of the dose. However, in case of rohitukine enriched fraction (A002-AEF) at 100 and 200 mg/kg (PO, QD) dose, significant reduction in serum TNF-alpha levels were observed (FIG. 6). Furthermore, A002-AEF at 100 mg/kg showed significant decrease in clinical symptoms (rat paw edema) compared to vehicle on day 10 of treatment; whereas there was no statistically significant decrease in clinical symptoms with A002-A.

The result of this study has clearly indicated the benefit of rohitukine-enrichment in the extract. The natural product 'rohitukine' at 5-15 mg/kg (PO) doses could not inhibit serum TNF-alpha; however enriched fraction (A002-AEF, contain 5% w/w rohitukine) at 100 and 200 mg/kg doses (which corresponds to 5 and 10 mg/kg dose of rohitukine) displayed statistically significant inhibition of serum TNF-alpha. The possible reason for this effect could be attributed to the presence of another natural product ' Schumaniofioside A' (9.7% w/w) in the enriched fraction which also has its own inhibitory effect on proinflammatory cytokine TNF-alpha. In case of enriched fraction, the synergistic effect of rohitukine, schumaniofioside A along with other natural products must be playing a crucial role in its efficacy in this in-vivo model (FIG. 6).

ADVANTAGES OF THE INVENTION

The main advantages of the present invention are:
1. Novel formulations provides sustained release of active ingredients in gastrointestinal tract for about 16-24 hrs, resulting in improved prolonged systemic availability of active ingredient.
2. An improvement in therapeutic effectiveness
3. Reduction in drug loss/dose frequency
4. The novel formulations provide prolonged and steady plasma concentration of rohitukine over 24 hours and thus it can help avoid under-dosing between dosage intervals.
5. The enriched fraction showed superior in-vivo effect on pro-inflammatory cytokines than hydroalcoholic extract.
6. The novel formulations are free-flowing and non-hygroscopic.
7. The excipients/polymers used in the formulations are within the acceptable limits.
8. Rohitukine-rich *Dysoxylum binectariferum* extract is capable of strongly inhibiting proinflammatory cytokines.

We claim:
1. A sustained release formulation comprising granules, said granules comprising:
   30-60% w/w of an extract or fraction obtained from leaves of *Dysoxylum binectariferum*;
   25-50% w/w of hydroxypropylmethylcellulose;
   5-15% w/w of sodium alginate; and
   a binder;
   wherein the extract or fraction comprises at least 2% w/w of Rohitukine and at least 1% w/w of Schumaniofioside A.

2. The sustained release formulation according to claim 1, wherein the extract is a hydroalcoholic extract.

3. The sustained release formulation according to claim 1, wherein the granules comprises a fraction obtained from leaves of *Dysoxylum binectariferum*, and the fraction is a soluble portion of a methanol:acetone system of the extract.

4. The sustained release formulation according to claim 1, wherein the hydroxypropylmethylcellulose is hydroxypropylmethylcellulose K4M or hydroxypropylmethylcellulose K15M.

5. The sustained release formulation according to claim 1, wherein the hydroxypropylmethylcellulose is hydroxypropylmethylcellulose K15M.

6. The sustained release formulation according to claim 1, wherein a total in-vitro dissolution time of said formulation required for release of 60-100% of rohitukine is between 16-24 hours.

7. The sustained release formulation according to claim 1, wherein the binder is selected from the group consisting of polyvinylpyrrolidone K 30 and polyvinylpyrrolidone K15.

8. The sustained release formulation according to claim 1, wherein the said formulation is in the form of a hard gelatin capsule or a tablet.

9. The sustained release formulation according to claim 1, wherein a total in-vitro dissolution time of said formulation required for release of 88-100% of rohitukine is between 16-24 hours.

10. A sustained release formulation comprising granules, said granules comprising:
    30-60% w/w of an extract or fraction obtained from leaves of *Dysoxylum binectariferum*;
    25-50% w/w of hydroxypropylmethylcellulose;
    5-15% w/w of sodium alginate; and
    a binder;
    wherein the extract or fraction comprises 2.6-13% w/w of Rohitukine and 0.5-10% w/w of Schumaniofioside A.

11. The sustained release formulation according to claim 10, wherein the granules comprise an extract obtained from leaves of *Dysoxylum binectariferum*, the extract comprising 2.6-7.8% w/w of rohitukine and 0.55-5% w/w of schumaniofioside A.

12. The sustained release formulation according to claim 10, wherein the granules comprise a fraction obtained from leaves of *Dysoxylum binectariferum*, the fraction comprising 5-13% w/w of rohitukine and 4-10% w/w of schumaniofioside A.

13. The sustained release formulation according to claim 1, wherein the formulation exhibits a rohithukine release half-life ($T_{50\%}$) of about 4 hours.

14. The sustained release formulation according to claim 1, wherein the formulation exhibits a $T_{75\%}$ rohitukine release of about 8 to about 10 hours.

* * * * *